United States Patent [19]

Brown

[11] 4,234,718
[45] Nov. 18, 1980

[54] PROCESS FOR PREPARING CELLULOSE ACETATE

[75] Inventor: David Brown, Greenwich, Conn.

[73] Assignee: Halcon Research and Development Corp., New York, N.Y.

[21] Appl. No.: 53,611

[22] Filed: Jun. 29, 1979

[51] Int. Cl.³ .................... C07B 53/08; C07C 51/15; C07C 51/54; C08B 3/06

[52] U.S. Cl. .................... 536/69; 260/546; 260/549; 536/71; 562/550; 562/607

[58] Field of Search .................... 536/69, 71; 260/546, 260/549; 562/550, 607

[56] References Cited

U.S. PATENT DOCUMENTS

| | | | |
|---|---|---|---|
| 2,136,030 | 11/1938 | Stone | 536/69 |
| 2,353,255 | 7/1944 | Malm et al. | 536/69 |
| 2,521,916 | 9/1950 | Hincke et al. | 536/69 |
| 2,632,007 | 3/1953 | Blume et al. | 536/69 |
| 2,635,097 | 4/1953 | Stoneman | 536/69 |
| 2,772,944 | 12/1956 | Allewelt | 536/71 |
| 2,801,237 | 7/1957 | Clevy et al. | 536/69 |
| 2,861,069 | 11/1958 | Touey et al. | 536/69 |
| 4,002,677 | 1/1977 | Naglieri et al. | 260/546 |
| 4,002,678 | 1/1977 | Naglieri et al. | 260/549 |
| 4,046,807 | 9/1977 | Kuckertz | 260/549 |
| 4,115,444 | 9/1978 | Rizkalla | 260/549 |

Primary Examiner—Ronald W. Griffin
Attorney, Agent, or Firm—William C. Long; David Dick; Riggs T. Stewart

[57] ABSTRACT

Cellulose acetate is produced from methanol, carbon monoxide and cellulose in an integrated series of steps wherein acetic anhydride produced in a first step by the carbonylation of methyl acetate is used to acetylate cellulose to produce cellulose acetate and to co-produce acetic acid is converted to ketene, the ketene is reacted with methanol to produce methyl acetate which is then fed to the first step and carbonylated to produce additional quantities of acetic anhydride.

6 Claims, 1 Drawing Figure

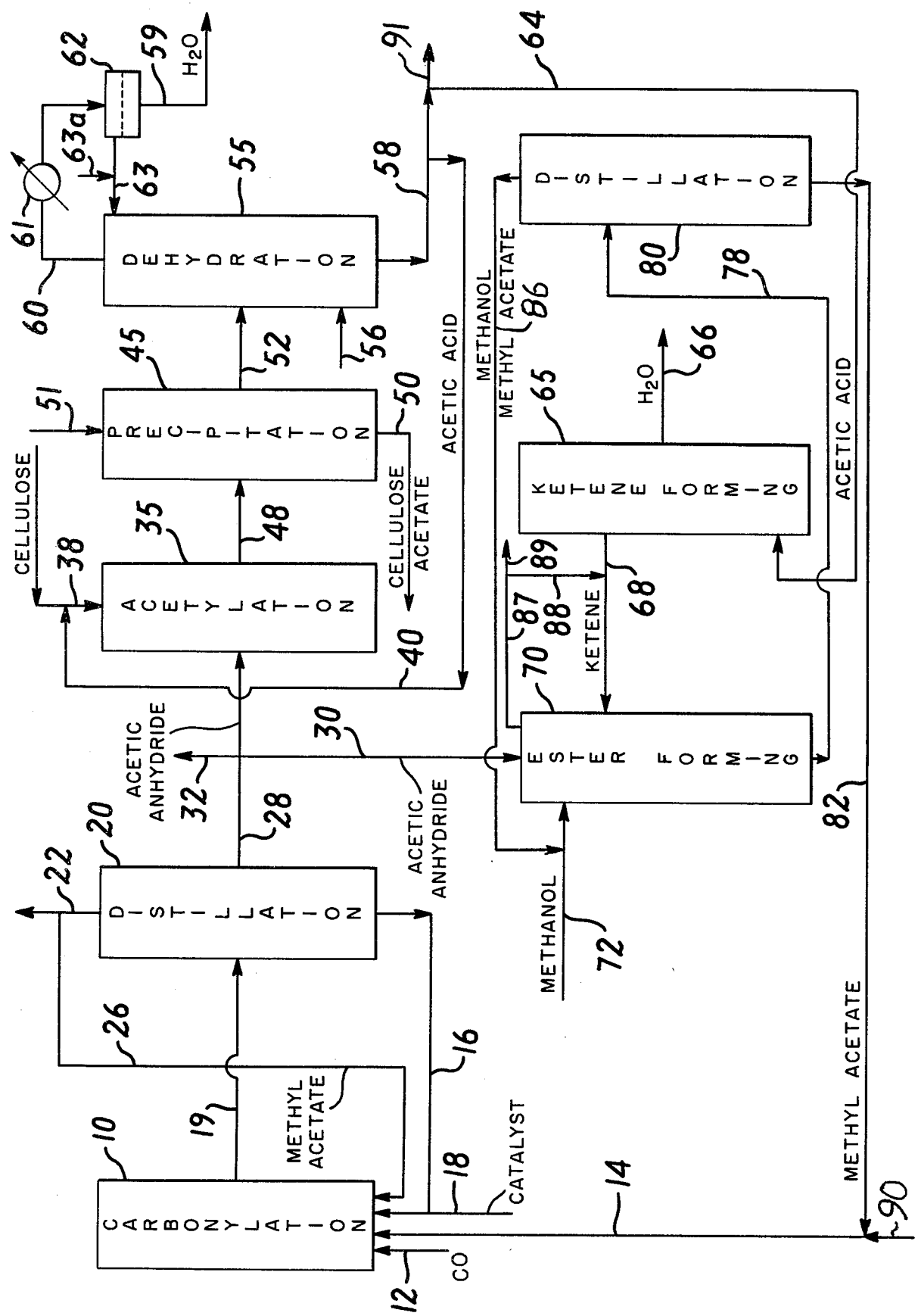

PROCESS FOR PREPARING CELLULOSE ACETATE

This invention relates to the preparation of cellulose acetate and is more particularly concerned with a process for producing cellulose acetate in an integrated series of steps which permit the production of this ester from methanol, carbon monoxide and cellulose.

Cellulose acetate is a well-known industrial product which has been produced for many years in large quantities. It has commonly been produced on an industrial scale by the reaction of acetic anhydride upon cellulose in various forms, e.g., cotton linters, wood pulp and corresponding forms of raw cellulose, or fibers formed from regenerated cellulose, or textiles formed from such fibers, or the like. In each case, the cellulose molecules are acetylated to the desired degree by means of acetic anhydride, the acetic anhydride being produced by supplying acetic acid which is converted to ketene and the ketene then converted to the desired anhydride by treatment with acetic acid.

It is an object of this invention to provide a novel process for producing cellulose acetate wherein the raw materials, other than cellulose, are methanol and carbon monoxide.

In accordance with the invention, acetic anhydride is produced by the carbonylation of methyl acetate in an anhydrous system, the so-produced acetic anhydride is reacted with a cellulose substrate to produce cellulose acetate and to co-produce acetic acid and the co-produced acetic acid is converted to methyl acetate which is supplied to the carbonylation step wherein acetic anhydride is produced, and the cycle is repeated.

More specifically, the co-produced acetic acid is converted to ketene and the ketene is reacted directly with methanol to produce methyl acetate, and the thus-produced methyl acetate is reacted with carbon monoxide to form acetic anhydride. Thus, the cellulose acetate is produced solely from methanol, carbon monoxide and cellulose and there is no need for a feed of acetic acid to the system. There is, therefore, made possible the production of cellulose acetate from methanol, carbon monoxide and cellulose in a fully integrated system, the methanol and carbon monoxide alone being the source of the acetate moiety in the product cellulose acetate, with net by-product acetic acid produced only as desired.

The invention will be more readily understood by reference to the accompanying drawing which shows, diagrammatically, and solely for purposes of facile exemplification, a typical reaction system for carrying out the process of the invention. Thus, referring to the drawing, the reference numerial 10 designates a carbonylation zone, which may comprise one or more pressure reactors of any convenient type, which is fed with carbon monoxide and methyl acetate along with recycle streams and which contains a suitable catalyst, typically one comprising a metal of Group VIII of the Periodic Table, in combination with iodine or bromine moieties, generally in a liquid-phase reaction system. Thus, carbon monoxide, in pure or diluted form, is supplied via line 12 and the methyl acetate enters via line 14. The catalyst, if removed with the reaction effluent, is recycled, as will be described below, via line 16, and make-up catalyst components are supplied, as needed, via line 18. The carbonylation can be effected batch-wise, if desired, but it will be apparent that it can be readily carried out continuously and, for commercial purposes, continuous operation is preferred. The same is true for the subsequent steps of the process of the invention which will be described below. Carbonylation is typically carried out at temperatures of 20° C. to 500° C., preferably 100° to 300° C. under a carbon monoxide partial pressure of 0.1 to 15,000 psi.

From zone 10, the reaction mixture is withdrawn via line 19 and is separated into its principal components. For this purpose the mixture is passed to a distillation zone 20 which is defined by one or more distillation units, e.g., flash and/or fractional distillation devices, as will be apparent to persons skilled in the art. If the carbonylation zone is operated in typical manner entirely in the liquid phase, the entire reaction mixture, including the Group VIII catalyst, is removed for separation. On the other hand, if the carbonylation is carried out as a boiling reaction, the effluent will be in the vapor phase and the relatively non-volatile catalyst will remain in the boiling liquid body in the carbonylation zone. The low-boiling components of the mixture, including methyl acetate, methyl iodide, and the like are removed through line 22, and suitably at least partially recycled via line 26 to carbonylation zone 10. The high boiling components of the reaction mixture, including the essentially non-volatile catalyst components, if present, are recycled to carbonylation zone 10 via previously-mentioned line 16 which communicates with line 18. The product acetic anhydride is withdrawn through line 28. A portion of the acetic anhydride thus separated can be diverted through line 30 to be used in the ester-forming reaction to be described below to produce methyl acetate to be used as feed to the carbonylation reaction. If it is desired to withdraw acetic anhydride as a co-product, this can be effected through line 32.

The bulk of the acetic anhydride in line 28 proceeds to the next step of the process for the eventual production of the desired cellulose acetate. In this step, the acetic anhydride is brought into contact in zone 35 with cellulose supplied to zone 35 through line 38, in the presence of acetic acid fed via line 40. Suitably, the cellulose to be treated is first activated by pre-soaking in acetic acid from line 40, e.g. for 10 minutes to 10 hours at 20° to 50° C. typically for about 1–2 hours at about room temperature, in accordance with conventional practice, the amount of acid being 0.25–10 parts by weight per part of cellulose, typically about 1–8 parts per part, preferably in the presence of a small amount of the catalyst to be used in the cellulose acetate forming reaction, e.g. sulfuric acid, benzene sulfuric acid, an acid-reacting ion exchange resin, and the like, although the use of the catalyst is not necessary. The activated or pre-soaked cellulose then passes via line 38 to acetylation zone 35.

In zone 35 the acetic anhydride produced as above described and the cellulose are brought together in the presence of an acetylation catalyst in order to effect acetylation of the cellulose by means of the acetic anhydride in conventional manner.

In the acetylation zone, the cellulose is acetylated by the acetic anhydride in the presence of a catalyst and in the presence of a solvent. In accordance with this invention, the solvent is most suitably acetic acid which is fed to the acetylation zone via line 40. The acetic acid can be mixed with the acetic anhydride prior to introduction into zone 35 or the acid and the anhydride can be added separately, the catalyst preferably being fed with the acetic acid. The ratio of acetic anhydride and solvent, e.g. acetic acid, can vary, as is well-known to persons skilled in the art, but typically the acetic anhydride is at least half of the quantity of acetic acid, including the acetic acid used in the pre-treatment, and can range up to about 10 parts by weight per part of acetic acid. Indeed, when large amounts of acetic acid have been used in the pre-treatment, only acetic anhydride and catalyst are added to the pre-treated cellulose and additional acetic acid solvent is not required. The amount of acetic anhydride is that which is conventionally used in this art and generally is in the range of 3 to 4 parts per part of cellulose. When the acetylation is carried out batch-wise, e.g. in a mixer of the Werner-Pfleiderer type, which has cooled mixing blades and cooled walls, the reaction liquid comprising the acetic anhydride, acetic acid and catalyst is preferably supplied step-wise in order to avoid excess heat generation and the liquid and the cellulose are thoroughly mixed until the desired degree of acetylation is achieved. The amount of catalyst can vary as is well-known to persons skilled in the art but is typically 1-5 percent by weight of the cellulose.

The degree of acetylation is then adjusted as desired in conventional manner by hydrolysis if less than fully acetylated cellulose acetate is desired, and the cellulose acetate is precipitated by means of dilute aqueous acetic acid in known manner in a zone or zones diagrammatically represented in the drawing as precipitation zone 45. The precipitated cellulose is separated from the aqueous acetic acid and withdrawn via line 50 for eventual washing and drying in accordance with known techniques. Precipitation dilutes the acetic acid contained in the reaction mixture and it is further diluted when the precipitated cellulose recovered from the reaction mixture is washed with water to remove reaction liquid. The treatment of the recovered cellulose is effected in conventional manner well-known to persons skilled in the art and such treatment is not involved in the process of this invention. Part of the dilute acetic acid thus recovered is recycled to the precipitation step to precipitate additional quantities of cellulose acetate and the remainder of the dilute acetic acid is then concentrated or dehydrated by distillation, most suitably azeotropic distillation in conventional manner.

Thus, the liquid effluent from precipitation zone 45, primarily comprising dilute aqueous acetic acid, some of which is suitably returned to zone 45 to precipitate further quantities of cellulose acetate, as mentioned, is passed via line 52 to dehydration zone 55 in which the acetic acid is dehydrated, e.g. by azeotropic distillation, to produce glacial acetic acid. In zone 55, which may consist of one or more distillation columns, the dilute aqueous acetic acid from precipitation zone 45, supplemented by dilute acid from the washing of the cellulose acetate withdrawn via line 50, the last-named dilute acid entering through line 56, is recovered in substantially anhydrous form for use in preparing methyl acetate and for recycling to the acetylation reaction. The dehydrated acetic acid is withdrawn through line 58 and the removed water is withdrawn via line 59. Most suitably the dehydration of the aqueous acetic acid is effected by azeotropic distillation in conventional manner, the azeotropic distillate being removed through line 60, condensed in condenser 61 and allowed to phase separate in separator 62, the azeotropic agent phase being withdrawn via line 63 and returned as reflux to dehydration zone 55 and the water phase being removed, as mentioned via line 59. Make-up azeotropic agent can be added to line 63 as indicated at 63a.

The acetic acid in line 58, is partly recycled via line 40 and some or all of the balance used to form methyl acetate as feed for the carbonylation in zone 10. Thus, the acetic acid from line 58 is supplied to line 64 which feeds it to ketene forming unit 65 in which the acetic acid is converted into ketene in conventional manner, using a ketene furnace of any convenient type well-known to persons skilled in the art. The thus-formed ketene is then passed via line 68 to ester-forming zone 70 where it is brought into contact with methanol supplied through line 72. The reaction product comprising methanol and methyl acetate is then passed via line 78 to distillation zone 80 wherein by fractional distillation the methanol and some methyl acetate are distilled away from the bulk of the methyl acetate which passes via line 82 to line 14 for feeding to the carbonyltion zone 10. The overhead mixture of methanol and methyl acetate are withdrawn via line 86 and condensed and recycled to ester-forming zone 70. Unreacted ketene is removed via line 87 and recycled via line 88 or some or all of the unreacted ketene may be withdrawn via line 89. Additional methyl acetate, if desired, is supplied to line 14 via line 90. Excess acetic acid in line 58 is withdrawn via line 91.

As previously mentioned, the carbonylation reaction involving methyl acetate and carbon monoxide which is carried out in carbonylation zone 10 if facilitated by a catalyst, most suitably a Group VIII metal, for example, a Group VIII noble metal, i.e. rhodium, iridium, ruthenium, palladium, osmium and platinum, as disclosed in Belgian Pat. Nos. 819,455 and 839,322, or a nickel catalyst as described in U.S. Pat. Nos. 4,002,677 and 4,002,678. The disclosures of these two U.S. patents are incorporated herein by reference. Thus, in the case of a Group VIII noble metal catalyst, the Group VIII noble metal can be employed in any convenient form, viz. in the zero valent state or in any higher valent form. For example, the catalyst may be the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Complexes of the metals can be employed, e.g. the metal carbonyls, such as iridium and rhodium carbonyls, e.g. hexarhodium hexadecacarbonyl, or as other complexes such as the carbonyl halides, e.g. iridium tri-carbonyl chloride $[Ir(CO)_3Cl]_2$ or chlorodicarbonyl rhodium dimer, or the acetylacetonates, e.g. rhodium acetylacetonate $Rh(C_5H_7O_2)_3$. It will be understood that the foregoing compounds and complexes and classes of compounds and complexes are merely illustrative of suitable forms of the Group VIII noble metal catalyst and are not intended to be limiting.

The metal employed may contain impurities normally associated with the commercially available metal or metal compounds, and need not be purified any further. Thus, the commercially available metal or metal compound is suitably employed.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 100,000 mols of ester, preferably 1 mol per 100 to 10,000 mols of ester, and most preferably 1 mol per 500 to 2,000 mols of ester.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like the other reactants, should, however, be essentially dry, i.e., the CO and the other reactants should be reasonably free from water. The presence of minor amounts of water such as may be found in the commercial forms of the reactants is, however, acceptable. Hydrogen, which may be present in very small (trace) amounts as an impurity, is not objectionable and even may tend to stabilize the catalyst.

It has been previously found that the activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of Groups IA, IIA and IIIA as are metals of Group VIB and the non-noble metals of Group VIII. In general, the most suitable elements are lithium, magnesium, calcium, titanium, chromium, iron, nickel and aluminum. Most preferred are lithium, aluminum and calcium, especially lithium. The promoters may be used in their elemental form, e.g. as finely-divided or powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts of organic mono-carboxylic acids, e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts, e.g. salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g. as a finely-divided metal, a slight induction period is observed.

The quantity of promoter can vary widely but preferably it is used in the amount of 0.0001 mol to 100 mols per mol of Group VIII noble metal catalyst, most preferably 0.001 to 10 mols per mol of catalyst.

In the working up of the reaction mixtures, e.g. by distillation, as discussed above, the promoter generally remains with the Group VIII metal catalyst, i.e. as one of the least volatile components, and is suitably recycled or otherwise handled along with the catalyst.

The activity of the Group VIII noble metal catalysts described above is also significantly improved, particularly with respect to reaction rate and product concentration, catalyst stability and corrosion inhibition, by the concurrent use of a promoter combination or co-promoter system containing a metal component which is a metal of Groups IVB, VB and VIB, and the non-noble metals of Group VIII, in any of the forms described above, in association or combination with an organo-nitrogen compound or an organo-phosphorus compound wherein the nitrogen and the phosphorus are trivalent.

The organic co-promoter can, in its broader sense, be any organo-nitrogen or organo-phosphorus compound wherein the nitrogen and phosphorus are trivalent. Preferably, however, the organo-nitrogen co-promoter is an amine, especially a tertiary amine of the formula

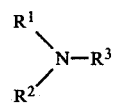

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine tetraacetic acid, and the like, or a heterocyclic amine such as pyridine, picoline, quinoline, methylquinoline, hydroxy quinoline, pyrrole, pyrrolidine, pyrrolidone, and the like, or an imidazole, such as imidazole, methyl imidazole and the like, or an imide of a carboxylic acid which may be monobasic or polybasic and which may be aliphatic or aromatic and preferably contains up to 20 carbon atoms, such as acetic acid, succinic acid, phthalic acid, pyromellitic acid, e.g. N,N-dimethylacetamide, succinimide, phthalimide and pyromellitic diimide, or a nitrile or amide which may be aliphatic or aromatic and preferably contain up to 20 carbon atoms, e.g. acetonitrile, hexamethyl phosphoric triamide, and like imides, nitriles, and amides, or an oxime such as cyclohexanone oxime, and the like. It will be understood, however, that higher molecular weight promoters, e.g. polymeric forms of the organo-nitrogen compounds, may be used such as polyvinylpyridine, polyvinyl pyrrolidone, and the like.

The organo-phosphorus co-promoter is preferably a phosphine of the formula

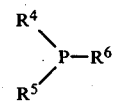

wherein $R^4$, $R^5$ and $R^6$ may be the same or different and are alkyl, cycloalkyl, aryl groups, amide groups or halogen atoms, preferably containing up to 1 to 20 carbon atoms in the case of alkyl and cycloalkyl groups and 6 and 18 carbon atoms in the case of aryl groups. Typical phosphines include trimethylphosphine, tripropylphosphine, tricyohexylphosphine and triphenylphosphine.

Although it is preferred that the organic promoters be added separately to the catalyst system, it is possible to add them as complexes with the Group VIII noble metal such as the trichloro trispyridine rhodium, tris(-triphenyl phosphine) rhodium, chlorotris (triphenyl phosphine) rhodium, and chlorocarbonyl bis (triphenyl phosphine) rhodium previously mentioned. Both free organic promoters and complexed promoters can also be used. Indeed, when a complex of the organic promoter and the Group VIII noble metal is used, it is desirable to add free organic promoter as well.

In accordance with a preferred embodiment of the invention, the carbonylation step is carried out in a single reaction zone to which a halide source, e.g. a hydrocarbyl halide such as methyl iodide, and the methyl acetate are both charged and are heated together, preferably in the liquid phase, in the presence of carbon monoxide and in the presence of the Group VIII metal catalyst. It will be understood that the hydrocarbyl halide may be formed in situ and the halide may thus be supplied to the system not only as the hydrocarbyl halide but the halogen moiety may also be supplied as another organic halide or as the hydro-halide or other inorganic halide, e.g. salts, such as the alkali metal or other metal salts, or even as elemental iodine or bromine.

As previously mentioned, in carrying out the carbonylation steps of the invention, a wide range of temperatures, e.g. 20° to 500° C. are suitable but temperatures of 100° to 300° C. are preferably employed and the more preferred temperatures generally lie in the range of 125° to 250° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but excessively high pressures, which require special high-pressure equipment, are not necessary. In general, the reaction is effectively carried out by employing a carbon monoxide partial pressure which is preferably 5 to 2,000 psi, although carbon monoxide partial pressures of 0.1 to 15,000 psi can also be employed. The total pressure is that required to provide the desired CO partial pressure and preferably that required to maintain the liquid phase. Typically, total pressures up to about 3,000 psig are used but most preferably they are at most about 1,000 psig. The reaction can be advantageously carried out in an autoclave or similar apparatus.

The ratio of ester to the halide in the reaction system can vary over a wide range. Typically, there are used 1 to 500 equivalents of the ester per equivalent of halide, preferably 1 to 200 equivalents per equivalent. Thus, there are typically used 1 to 500 mols, preferably 1 to 200 mols of ester per mol of halide reactant. By maintaining the partial pressure of carbon monoxide at the values specified, adequate amounts of the reactant are always present to react with the hydrocarbyl halide.

The effluent from the carbonylation step is treated, e.g. distilled, by conventional techniques to separate the product acetic anhydride from it and to recover streams containing unreacted methyl acetate, iodine moieties, catalyst components (and promoter components, if employed), all of which are recycled to the carbonylation reaction for reuse. As indicated above, the distillation of the carbonylation effluent is conveniently effected in one or more distillation units, e.g. flash and/or fractional distillation devices, represented in the drawing by distillation zone 20. In distillation zone 20 temperatures of 50° to 180° C. and pressures of 0 to 60 psig typically prevail.

The reaction of the acetic anhydride with the cellulose and the recovery of the product cellulose acetate and the coproduced acetic acid, including the dehydration of the dilute acetic acid streams to produce concentrated glacial acetic acid, are, as previously mentioned, readily carried out in known manner in accordance with conventional techniques with which a person skilled in the art is fully familiar. With respect to the acetylation of cellulose, in addition to the description above, additional examples of suitable processes can be found, for instance, in Stone U.S. Pat. No. 2,136,030, Malm et al. U.S. Pat. No. 2,353,255, Hincke U.S. Pat. No 2,521,916, Blume et al. U.S. Pat. No. 2,632,007, Stoneman U.S. Pat. No. 2,635,097 and Touey et al. U.S. Pat. No. 2,861,069. While the foregoing patents refer primarily to batch operations, continuous processes for acetylating cellulose are well-known to persons skilled in the art and in this connection, reference is made to Clevy et al. U.S. Pat. No. 2,801,237.

With regard to recovery of concentrated or glacial acetic acid from the dilute acetic acid streams which are obtained as a result of the acetylation reaction and the treatment of the acetylated product, i.e., the cellulose acetate, azeotropic distillation is the method of choice. The dehydration of acetic acid by azeotropic distillation is a well-known process and various effective azeotropic agents can be used, such as benzene, ketones, e.g., ethyl propyl ketone, and dipropyl ketone and ethers such as ethyl amyl ether and dibutyl ether, esters such as n-propyl acetate and i-propyl acetate, and the like. Typical processes of this type are disclosed in Othmer U.S. Pat. Nos. 2,028,800, 2,076,184, 2,170,834 and 2,184,563. Of course, it is also possible to effect the dehydration by other means such as extractive distillation as disclosed in Hartley U.S. Pat. No. 2,651,604 wherein a dimethoxy polyglycol, e.g. dimethoxy diethylene glycol, is used as the extractive distillation agent.

The conversion of the dehydrated or glacial acetic acid to ketene is suitable carried out by pyrolysis in a ketene furnace by known techniques.

Thus, the acetic acid is subjected to pyrolysis temperatures typically in the range of 700° to 800° C. under atmospheric pressure or subatmospheric pressures down to about 100 mmHg. in the presence of a catalyst such as triethyl phosphate, triethyl thionophosphate, sodium metaphosphate or other phosphoric acid salts. Solid supported forms such as carborundum coated with sodium metaphosphate can also be used. The pyrolysis is effected in a ketene furnace such as described in Painter et al. U.S. Pat. No. 2,776,192 or Painter U.S. Pat. No. 2,784,065. The vapors issuing from the ketene furnace are cooled down to about room temperature, e.g. with cold water as a cooling medium, so that by-product water together with unreacted or reformed acetic acid separate in the liquid state in the form of dilute acetic acid in the form of 30–40% strength. Owing to the reduced pressure under which the ketene furnace vapors are treated, part of the water and part of the acetic acid remain in the vapor phase. This is not objectionable since a small amount of water can readily be removed from the eventually formed methyl acetate prior to feeding it to the carbonylation zone. Indeed, some of the ketene may react with the acetic acid to form acetic anhydride which, of course, will react with the methanol in the ester-forming stage to form the desired methyl acetate. Thus, there is no need to purify the ketene in carrying out the process of this invention although the ketene can be purified if it is desired to do so for some reasons. Such purification can, for example, be effected by further cooling the ketene-containing gas to from about 0° to about −10° C. under a pressure between about 600 and about 2,000 mmHg., preferably a pressure of about atmospheric.

The ketene issuing from the ketene furnace is converted into methyl acetate by bringing it into contact with methanol in the presence of an appropriate catalyst, such as catalysts suitable for esterification reaction, preferably catalysts in solid form, e.g. an alumina-silica-zirconia catalyst or aluminum silicates having exchangeable cations, an acidic ion exchange resin, and the like. This reaction can be carried out at moderate temperatures of the order of 20°–80° C., preferably about 30°–50° C. merely by bringing the ketene and the alcohol into intimate contact, e.g. by counter-current flow in the presence of the catalyst. Any catalyst present in the effluent can be removed by filtration. The ketene in the ester-forming reaction can be supplemented by the addition of acetic anhydride fed via line 30 as shown in the drawing. Thus, it is possible to produce sufficient methyl acetate for feed to the carbonylation reaction without requiring the supply of methyl acetate from the outside so that the only reactants fed to the system are carbon monoxide, methanol and cellulose. Since substantially anhydrous methyl acetate is desired for the carbonylation reaction, if water is present in the methyl acetate, the methyl acetate is advantageously dehydrated by any convenient means, e.g. by solvent extraction, for example, as described in Curtis U.S. Pat. No. 3,904,676. Any acetic acid formed can accompany the methyl acetate to the carbonylation and recovered upon distillation of the carbonylation effluent. This acetic acid can, of course, be fed to the ketene-forming step. Alternatively, it can be separated from the methyl acetate before the latter is fed to the carbonylation reaction.

The liquid ester-forming effluent withdrawn via line 78 will comprise product methyl acetate and unreacted methanol. This mixture is readily separated in conventional manner by fractional distillation. Typically, the mixture is distilled at a pressure of 10–20 psia to separate as distillate a methanol-methyl acetate azeotrope from the remaining methyl acetate. The methanol-methyl acetate azeotrope is returned to the ester-forming step via line 86 for further reaction with ketene and the methyl acetate recovered via line 82 is supplied as feed to the carbonylation reaction previously described, after dehydration, if necessary as previously discussed.

As previously mentioned, it is possible to carry out the integrated cyclic process of this invention with feeds consisting essentially of methanol, carbon monoxide and cellulose. If acetic acid formed with the cellulose acetate is partly withdrawn for other uses via line 91 or is otherwise insufficient to provide, after conversion to ketene and reaction to the ketene with methanol, all of the methyl acetate for the carbonylation reaction, additional methyl acetate can readily be produced in the ester-forming zone from some of the acetic anhydride produced in the carbonylation zone in accordance with equation

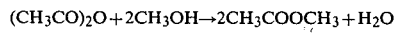

Of course, acetic acid and/or methyl acetate can be supplied from an external source if it is desired to remove all of the acetic anhydride not used for cellulose acetate formation in the system. It is preferred, however, to utilize some of this acetic anhydride to produce methyl acetate as described above or by converting it to acetic acid in accordance with the equation

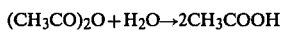

and supplementing the acetic acid in line 64 with the thus-produced acetic acid.

The following examples will serve to provide a fuller understanding of the invention, but it is to be understood that these examples are given for illustrative purposes only and are not to be interpreted as being limitative of the invention. In the examples, all parts are on a molar basis, unless otherwise indicated.

EXAMPLE I

Using an apparatus system such as illustrated in the drawing, a carbonylation zone 10 in the form of a stirred pressure reactor is filled to the level of withdrawal line 19 with a mixture composed of approximately 93.5 mol percent methyl acetate, 2.25 mol percent methyl iodide, 4 mol percent lithium iodide and 0.25 mol percent rhodium acetate. This mixture is heated to about 170° C. and carbon monoxide is introduced into the reactor to provide and maintain a partial pressure of carbon monoxide of 300 psi, resulting in a total pressure of about 500 psig. Continuous liquid feed to the reactor is then begun and liquid reaction product is withdrawn and distilled to separate a product acetic anhydride stream and to provide recycle streams containing some acetic anhydride as well as unreacted methyl acetate and iodine, lithium and rhodium values resulting from the methyl iodide, lithium iodide and rhodium acetate initially charged, the recycle streams being continuously returned to the reactor. The reactor is carried out to provide a residence time in the reactor of about three hours. Thus, there are continuously fed approximately 750 parts per hour of methyl acetate (including 490 parts recycle methyl acetate) along with recycle of the iodine, lithium and rhodium values representing 18 parts per hour of methyl iodide, 32 parts per hour of lithium iodide and 2 parts per hour of rhodium acetate, together with recycle acetic anhydride, the recycle streams being obtained as described below. The reaction mixture is continuously withdrawn at the rate of 1,000 parts per hour and passed into distillation zone 20. In distillation zone 20, the reactor effluent is first flashed at about 50 psia and 150° C. The heavy liquid from the flash, which contains the catalyst components, some methyl acetate and some acetic anhydride is recycled to carbonylation zone 10 at the rate of approximately 300 parts per hour. The vapor from the flash is fractionally distilled at a pressure of about 50 psia and at a temperature in the range of 50° to 160° C. to separate approximately 440 parts per hour of a "lights" fraction comprising methyl acetate and methyl iodide, which is recycled to carbonylation zone 10 via line 26. The bottoms from this distillation are comprised of approximately 260 parts per hour of product acetic anhydride which are fed via line 28 to acetylation zone 35 for reaction with cellulose in the presence of recycle acetic acid from line 40. Acetylation is carried out continuously as described in Clevy et al. U.S. Pat. No. 2,801,237, following the procedure described in the example, using cellulose, suitably in the form of cotton linters, impregnated with twice its weight of the recycle acetic acid. The feed of acetic anhydride is, as mentioned, approximately 260 parts per hour and the cellulose and the other components of the reaction system are supplied in amounts to provide the relative proportions set forth in the patent. Following the dilution of the reaction mixture with the mixture of 60% acetic acid and 40% water, the cellulose acetate is hydrolyzed and precipitated in conventional manner and then purified. Hydrolysis and precipitation are carried out in the usual way such as described on pages 339 and 340 of Volume 3 of the "Encyclopedia of Polymer Science and Technology" published by Interscience Publishers (1965). These steps are carried out batch-wise but by using a plurality of vessels in parallel and switching from one to the other, the continuous supply from the acetylation reactor and the continuous supply of dilute acetic acid to the dehydration step are readily accomodated.

The dilute acetic acid obtained from the hydrolysis and precipitation, combined with the dilute acetic acid obtained from washing the cellulose acetate, is then continuously dehydrated by azeotropic distillation with normal propyl acetate as described in Othmer U.S. Pat. No. 2,028,800. The dehydrated acetic acid thus produced is divided to provide a recycle stream which is returned via line 40 to supply acetic acid for impregnating the cellulose and for incorporation in the acetylation reaction mixture, as well as for hydrolysis and precipitation of the cellulose acetate. Additional so-recovered acetic acid provides approximately 260 parts per hour of acetic acid which is fed to line 64 and supplied to ketene-forming zone 65.

Conversion of acetic acid to ketene is carried out in the vapor phase under high temperature pyrolysis conditions as described in McKlveen U.S. Pat. No. 2,806,064, using a ketene furnace such as described in Painter U.S. Pat. No. 2,784,065. The purification step described by McKlveen is suitably employed but is not essential. The thus-produced ketene is then supplied via line 68 to ester-forming zone 70 into which are also introduced methanol in an amount corresponding to 260 parts per hour. At the same time, there is introduced a recycle stream composed of a methyl acetate-methanol azeotrope in an amount corresponding to a rate of 50 parts per hour. In ester-forming zone 70, the ketene is converted to methyl acetate by the process described in Matthias et al. U.S. Pat No. 3,723,509. Unreacted gases are withdrawn via line 87 and recycled via line 88 and 68 or they can be withdrawn and returned to the ketene-forming step in the manner described in Eberts et al. U.S. Pat. No. 2,688,635. The reaction mixture formed in ester-forming zone 70 consisting essentially of methyl acetate and methanol is supplied via line 78 to fractional distillation zone 80 in which there is distilled as overhead by ordinary fractional distillation, the above-mentioned methanol-methyl acetate azeotrope which is recycled to the ester-forming operation via line 90. The bottoms from this distillation consist of methyl acetate and any small amounts of water, acetic acid and acetic anhydride which may be present. This stream is substantially dehydrated and then fed to carbonylation zone via line 82 to provide the necessary feed to the carbonylation zone as previously described.

In the operations described above involving the conversion of acetic acid to methyl acetate, there are normally some processing and related losses with the result that the amount of methyl acetate produced will be less than that needed to supply the total quantity of methyl acetate required for the carbonylation zone. This, shortfall of methyl acetate can, of course, be compensated for by supplying make-up methyl acetate as required. It is a feature of the invention, however, that the process can effectively be carried out using only carbon monoxide, cellulose and methanol as feed materials. The following example illustrates how any short-fall in methyl acetate availability can be readily met without requiring make-up methyl acetate from an external source. This is done by producing more acetic anhydride than is required to be fed to the cellulose acetylation step and using this acetic anhydride to supplement the acetic acid from the cellulose acetate-producing operation as well as to supply by-product acetic anhydride, if desired.

EXAMPLE II

Using the apparatus system described in Example I, carbonylation zone 10 is continuously fed as described in Example I but with 300 parts per hour of methyl acetate plus 490 parts per hour of recycle methyl acetate and the reaction mixture is maintained at a temperature of about 170° C. and carbon monoxide is continuously introduced to maintain a partial pressure of carbon monoxide of 300 psi and a total pressure of 500 psig, as described in Example I. The reaction mixture is withdrawn at the rate of approximately 1,040 parts per hour and distilled in distillation zone 20 under the conditions described in Example I. As a result of such distillation there are obtained approximately 300 parts per hour of acetic anhydride, 260 parts per hour of which are supplied to the acetylation zone 35, 20 parts per hour are withdrawn via line 32 and the remaining 20 parts per hour are fed via line 39 to esterification zone 70. The acetylation, hydrolysis, precipitation, dehydration and ketene-forming are carried out as described in Example I, the acetic acid in line 64 being supplemented by acetic acid obtained by hydrolyzing the acetic anhydride from line 32 (40 parts per hour of acetic acid). In the ester-forming step, ester-forming zone 70 is fed with 300 parts per hour of methanol via line 72. As a result of the formation of methyl acetate from the supplemented acetic acid and the acetic anhydride, there are produced 300 parts per hour of methyl acetate which are required in the esterification step. Notwithstanding the processing and other losses, the additional acetic acid compensates for the losses and the full 300 parts per hour of methyl acetate are available for forwarding to carbonylation zone 10. A corresponding supply of supplemental acetic acid moieties can be provided by feeding acetic anhydride from line 32 directly to ester-forming zone 70.

What is claimed is:

1. A cyclic integrated process for the preparation of cellulose acetate from methanol, cellulose and carbon monoxide which comprises the steps of:
    (1) carbonylating methyl acetate to produce acetic anhydride in a carbonylation zone;
    (2) reacting at least some of the so-produced acetic anhydride with cellulose to convert at least part of said acetic anhydride to cellulose acetate and acetic acid;
    (3) converting said acetic acid to ketene;
    (4) reacting said ketene with methanol in an ester-forming zone to form methyl acetate for step (1); and
    (5) introducing methyl acetate produced in step (4) into said carbonylation zone.

2. A process as defined in claim 1, wherein at least a portion of said acetic anhydride produced in said carbonylation zone is introduced into said ester-forming zone for reaction with said methanol to produce methyl acetate.

3. A process as defined in claim 1, wherein step (1) is carried out in the presence of a catalyst comprising a Group VIII metal.

4. A process as defined in claim 3, wherein the catalyst comprises a Group VIII noble metal.

5. A process as defined in claim 3, wherein the catalyst comprises nickel.

6. A process as defined in claim 1, wherein the methanol reacted with the ketene is a mixture of methanol and a methyl acetate-methanol azeotrope.

* * * * *